(12) United States Patent
Bonassar et al.

(10) Patent No.: US 6,773,713 B2
(45) Date of Patent: Aug. 10, 2004

(54) INJECTION MOLDING OF LIVING TISSUES

(75) Inventors: Lawrence J. Bonassar, Acton, MA (US); Jon A. Rowley, Chapel Hill, NC (US); David J. Mooney, Ann Arbor, MI (US)

(73) Assignee: University of Massachusetts, Boston, MA (US)

(*) Notice: Subject to any disclaimer, the term of this patent is extended or adjusted under 35 U.S.C. 154(b) by 57 days.

(21) Appl. No.: 10/081,897

(22) Filed: Feb. 21, 2002

(65) Prior Publication Data
US 2002/0159982 A1 Oct. 31, 2002

Related U.S. Application Data
(60) Provisional application No. 60/271,104, filed on Feb. 23, 2001.

(51) Int. Cl.[7] .............................. A61F 2/02; A61F 2/10; A61F 2/20; A61F 2/28
(52) U.S. Cl. ........................ 424/423; 424/424; 424/425; 424/426
(58) Field of Search ................................. 424/423, 424, 424/425, 426

(56) References Cited
U.S. PATENT DOCUMENTS

| | | | |
|---|---|---|---|
| 4,188,373 A | 2/1980 | Krezanoski | 424/78 |
| 4,352,883 A | 10/1982 | Lim | 435/178 |
| 4,474,751 A | 10/1984 | Haslam et al. | 424/78 |
| 4,474,752 A | 10/1984 | Haslam et al. | 424/78 |
| 4,474,753 A | 10/1984 | Haslam et al. | 424/78 |
| 4,478,822 A | 10/1984 | Haslam et al. | 424/78 |
| 4,659,524 A | 4/1987 | Neefe | |
| 5,410,016 A | 4/1995 | Hubbell et al. | 528/354 |
| 5,919,702 A | 7/1999 | Purchio et al. | |
| 6,051,249 A | 4/2000 | Samuelsen | |
| 6,129,761 A * | 10/2000 | Hubbell | 623/11 |
| 6,171,610 B1 | 1/2001 | Vacanti et al. | |
| 6,224,893 B1 * | 5/2001 | Langer et al. | 424/423 |

OTHER PUBLICATIONS

Abbott et al. "Computer Generated Mandibular Model: Surgical Role" *Aust. Dent. J.* 43:373–378 (1998).
Anbinder et al. "Anophthalmic Socket and Orbital Implants" *Radiol. Clin. North. Am.* 36:1133–1147 (1998).
Atala et al. "Endoscopic Treatment of Vesicoureteral Reflux with a Chondrocyte–Alginate Suspension" *J. of Urol.* 152(2 Pt 2):641–643; discussion 644 (1994).
Atala et al. "Injectable Alginate Seeded with Chondrocytes as a Potential Treatment for Vesicoureteral Reflux" *J. of Urol.* 150(2 Pt 2):745–747 (1993).
Beekman et al. "Synthesis of Collagen by Bovine Chondrocytes in Alginate; Posttranslational Modifications and Cell–Matric Interaction" *Exper. Cell Res.* 237(1):135–141 (1997).
Cadee et al. "*In vivo* Biochompatibility of Dextran–Based Hydrogels" *J. of Biomed. Mat. Res.* 50:397–404 (2000).
Cao et al. "Comparative Study of the Use of Poly (Glycolic Acid), Calcium Alginate and Pluronic in the Engineering of Autologous Porcine Cartilage" *J. Biomater. Sci. Polymer Edn.* 9(5):475–487.

(List continued on next page.)

*Primary Examiner*—Carlos A. Azpuru
(74) *Attorney, Agent, or Firm*—Fish & Richardson P.C.

(57) ABSTRACT

The invention features methods of making living tissue constructs having a predetermined shape by providing a negative mold having a defined shape; suspending isolated tissue precursor cells in a hydrogel to form a liquid hydrogel-precursor cell composition; introducing the liquid hydrogel-precursor cell composition into the mold; inducing gel formation to solidify the liquid hydrogel-precursor cell composition to form a living tissue construct; and removing the living tissue construct from the mold after gel formation.

20 Claims, 8 Drawing Sheets

OTHER PUBLICATIONS

Cao et al. "Tissue–Engineered Nipple Reconstruction" *Plast. Reconstr. Surg.* 102:2293–2298 (1999).

Cao et al. "Transplantation of Chondrocytes Utilizing a Polymer–Cell Construct to Produce Tissue–Engineered Cartilage in the Shape of a Human Ear" *Plast. Reconstr. Surg.* 100:297–302 (1997).

Cohen et al. "Biology of Implants Used in Head and Neck Surgery" *Facial Plast. Surg. Clin. N. Am.* 7:17–41 (1999).

Guo et al. "Culture and Growth Characteristics of Chondrocytes Encapsulated in Alginate Beads" *Connect. Tissue Res.* 19(2–4):277–297 (1989).

Hauselmann et al. "Phenotypic Stability of Bovine Articular Chondrocytes after Long–Term Culture in Alginate Beads" *J. Cell Sci.* 107:17–27 (1994).

Hauselmann et al. "Synthesis and Turnover of Proteoglycans by Humans and Bovine Adult Articular Chondrocytes Culture in Alginate Beads" *Matrix* 12(2):116–129 (1992).

Huband "Intranasal Conformers: A Case Report" *J. Dent. Technol.* 14:12–15 (1997).

Huggett et al. "Dimensional Accuracy and Stability of Acrylic Resin Denture Bases" *J. Prosthet. Dent.* 68:634–640 (1992).

Kapur et al. "Fabrication and Selective Surface Modification of 3–Dimensionaly Textured Biomedical Polymers from Etched Silicon Substrates" *J. Biomed. Mater. Res.* 33:205–216 (1996).

König et al. "Autosterlization of Biodegradable Implants by Injection Molding Process" *J. Biomed. Mater. Res.* 38:115–119 (1997).

Lovice et al. "Grafts and Implants in Rhinoplasty and Neal Reconstruction" *Otolaryngol. Clin. N. Am.* 32:113–139 (1999).

Marler et al. "Soft–Tissue Augmentation with Injectable Alginate and Syngeneic Fibroblasts" *Plastic and Reconstructive Surgery* 105:2049–2058 (2000).

Paige et al. "De Novo Cartilage Generation Using Calcium Aliginate–Chondrocyte Constructs." *Plast. Reconstr. Surg.* 97(1):168–178; discussion 179–180 (1996).

Paige et al. "Injectable cartilage" *Plast. Reconstr. Surg.* 96(6):1390–1398; discussion 1399–1400 (1995).

Peppas et al. "Hydrogels in Pharmaceutical Formulation" *European Journal of Pharmaceutics and Biopharmaceutics* 50:27–46 (2000).

Puelacher et al. "Design of Nasoseptal Cartilage Replacements Synthesized from Biodegradable Polymers and Chondrocytes" *Biomaterials* 15:774–778 (1994).

Sakata et al. "Tracheal Composites Tissue–Engineered from Chondrocytes, Tracheal Epithelial Cells and Synthetic Degradable Scaffolding" *Transplant. Proc.* 26:3309–3310 (1994).

Vacanti et al. "Experimental Tracheal Replacement Using Tissue–Engineered Cartilage" *Journal of Pediatric Surgery* 29:201–205 (1994).

Verstreken et al. "An Image–Guided Planning System for Endosseous Oral Implants" *IEEE Trans. Med. Imaging* 17:842–852 (1998).

Zimmermann et al. "Hydrogel–Based Non–Autologous Cell and Tissue Therapy" *BioTechniques* 29:564–581 (2000).

\* cited by examiner

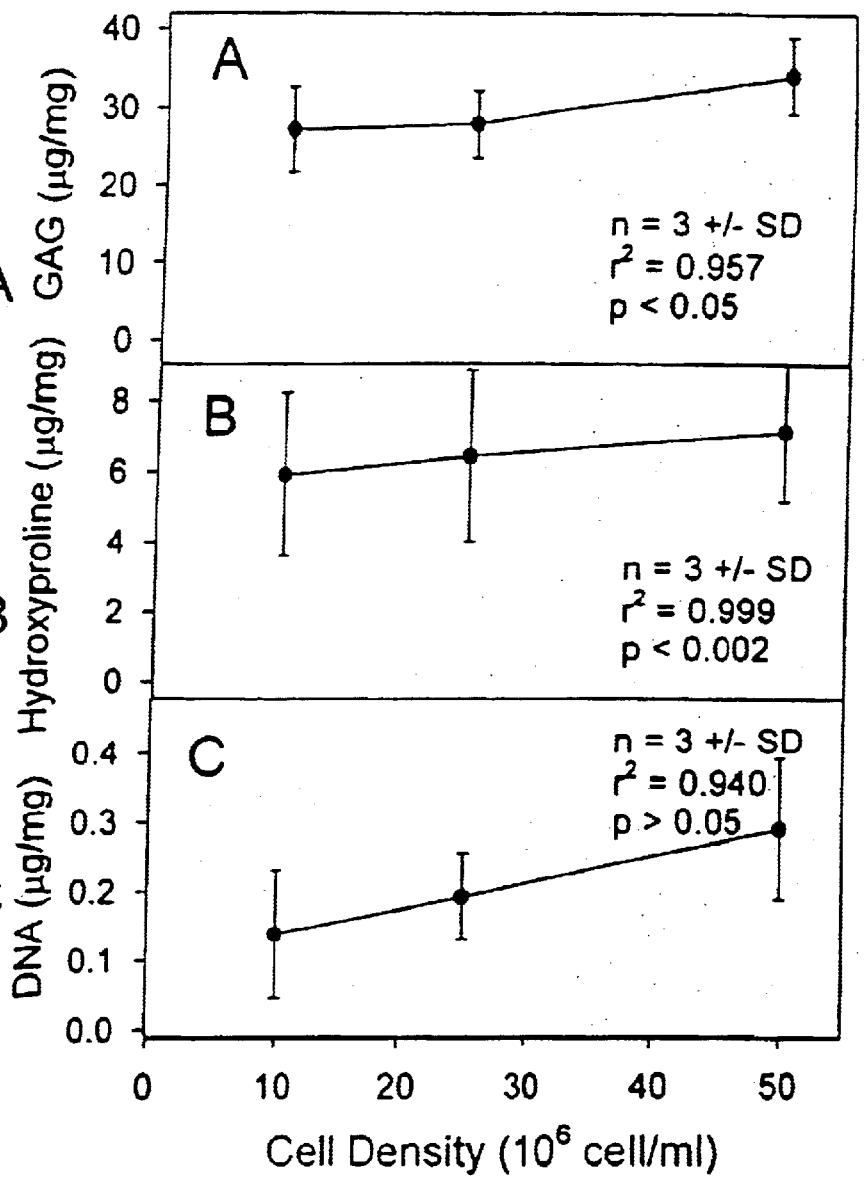

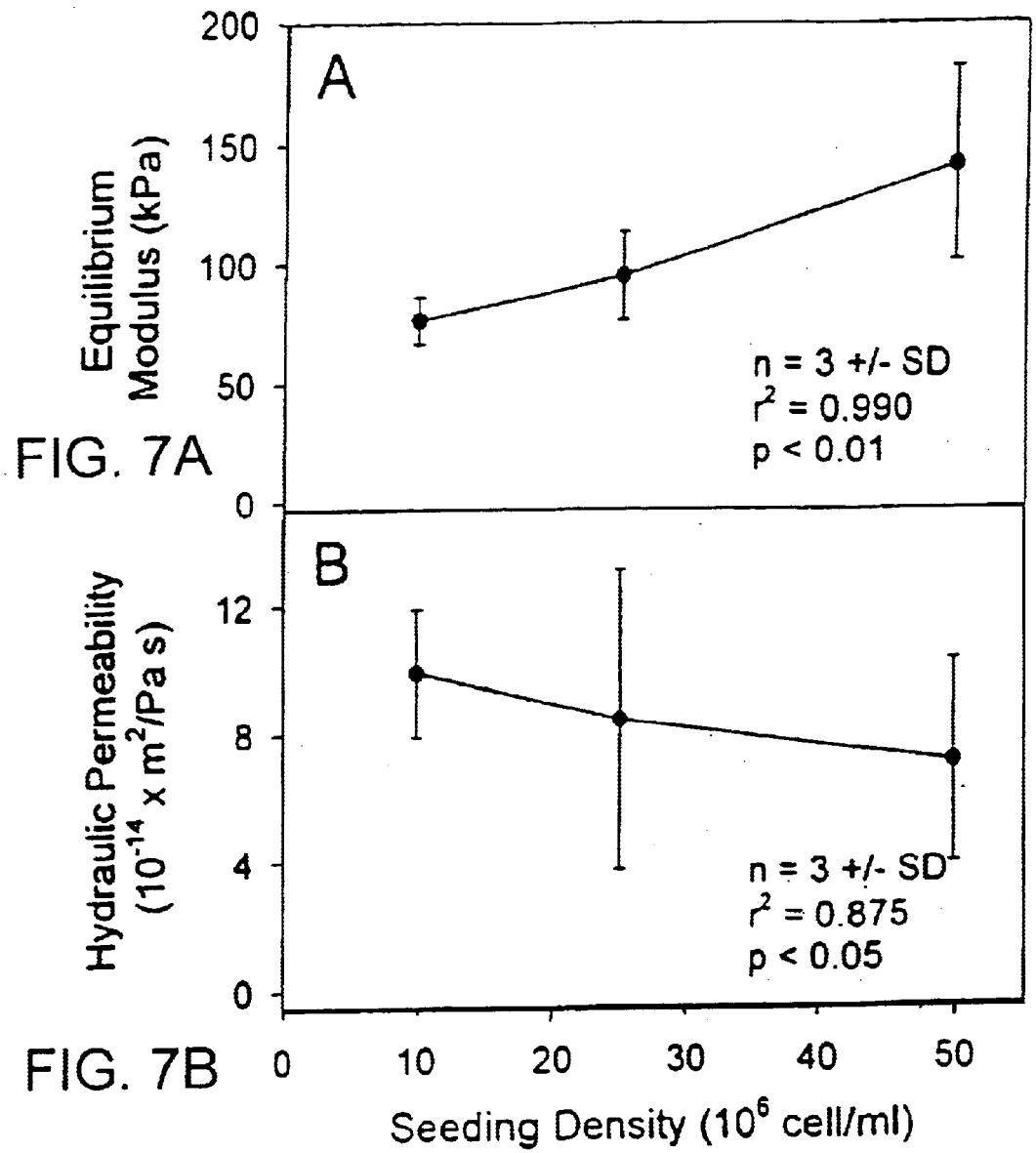

INJECTION MOLDING OF LIVING TISSUES

CROSS-REFERENCE TO RELATED APPLICATIONS

This application claims priority from U.S. Provisional Patent Application Serial No. 60/271,104, filed on Feb. 23, 2001, which is incorporated herein by reference in its entirety.

TECHNICAL FIELD

This invention relates to tissue engineering, materials science, cell biology, and plastic surgery.

BACKGROUND

Over one million surgical procedures in the United States each year involve bone and cartilage replacement (Langer et al., 1993, Science, 920:260–266). The reconstruction of the anatomy of the head and neck presents a considerable challenge because of the unique geometries of facial structures, which require a high degree of complexity and precision in implant fabrication. The use of allografts for these applications is limited by immunological complications, transmission of infectious diseases from the donor, premature resorption of the transplant, and lack of the ability and availability of donor material. Consequently, the use of autologous cartilage and/or bone grafts is considered a primary option. See, e.g., Lovice et al., 1999, Otolaryngol. Clin. N. Am., 32:113–139. However, tissues from locations such as the rib or iliac crest are limited in supply, are associated with significant donor site morbidity, and require significant surgical time to generate an appropriately shaped implant. The use of pre-shaped prosthetic implants made from materials such as polyethylene, silicon, or polytetrafluoroethylene (PTFE) is common, but can be complicated due to higher infection rates and eventual protrusion of implants at the site of the procedure (Cohen et al., 1999, Facial Past. Surg. Clin. N. Am., 7:17–41).

Tissue engineering involves the regeneration of tissues such as bone and cartilage by seeding cells onto a customized biodegradable polymer scaffold to provide a three dimensional environment that promotes matrix production. This structure anchors cells and permits nutrition and gas exchange with the ultimate formation of new tissue in the shape of the polymer material. See, e.g., Vacanti et al., 1994, Transplant. Proc., 26:3309–3310; and Puelacher et al., 1994, Biomaterials, 15:774–778.

SUMMARY

The invention is based on the discovery that industrial design and manufacturing techniques, such as injection molding, can be used to create detailed, three-dimensional living tissues.

In general, the invention features methods of making living tissue constructs having a specific, e.g., predetermined shape by providing a negative mold having a predetermined, three-dimensional shape; suspending isolated tissue precursor cells in a hydrogel to form a liquid hydrogel-precursor cell composition; introducing the liquid hydrogel-precursor cell composition into the mold; inducing, e.g., controllably inducing, gel formation to solidify the liquid hydrogel-precursor cell composition to form a living tissue construct; and removing the living tissue construct from the mold after gel formation. For example, the cells can be epidermal cells, chondrocytes and other cells that form cartilage, macrophages, adipocytes, dermal cells, muscle cells, hair follicles, fibroblasts, organ cells, osteoblasts, osteocytes and other cells that form bone, endothelial cells, mucosal cells, pleural cells, ear canal cells, tympanic membrane cells, peritoneal cells, Schwann cells, corneal epithelial cells, gingiva cells, central nervous system neural stem cells, or tracheal epithelial cells.

The hydrogels can be alginate (e.g., at a concentration of 0.5% to 8% or 1% to 4%, e.g., 2%), chitosan, pluronic, collagen, or agarose. The hydrogels can also be polysaccharides, proteins, polyphosphazenes, poly (oxyethylene)-poly(oxypropylene) block polymers, poly (oxyethylene)-poly(oxypropylene) block polymers of ethylene diamine, poly(acrylic acids), poly(methacrylic acids), copolymers of acrylic acid and methacrylic acid, poly(vinyl acetate), or sulfonated polymers. In these methods and depending on the hydrogel, gel formation can be induced by contacting the liquid hydrogel with a suitable concentration of a divalent cation, such as $Ca^{++}$, e.g., at a concentration of 0.2 g/ml of an alginate solution.

Once the construct is made, it can be directly implanted, or cultured, e.g., in vitro, to allow the cells to grow within the hydrogel construct, e.g., for a period of 1 to 30 days.

In another aspect, the invention features methods of reconstructing an anatomical feature in a mammal by providing a suitable negative mold having a three-dimensional negative shape of the anatomical feature; suspending isolated tissue precursor cells in a hydrogel to form a liquid hydrogel-precursor cell composition; introducing the liquid hydrogel-precursor cell composition into the mold; inducing gel formation to solidify the liquid hydrogel-precursor cell composition to form a living tissue construct; removing the tissue construct from the mold after gel formation; and implanting the tissue construct into the mammal. Alternatively, the method can include obtaining a living tissue construct having the three-dimensional shape of the anatomical feature; and implanting the tissue construct into the mammal. In this method, the construct can be prepared by the new methods described herein.

The invention also features the injection-molded living tissue constructs made by the new methods. These constructs can have a variety of shapes, e.g., they can be in the shape of particular cartilage adjacent a joint, a bone, a portion of a bone, or a bone defect.

A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the cells evenly suspended within a mold until the gel solidifies. The hydrogels are also biocompatible, e.g., not toxic, to cells suspended in the hydrogel.

A "hydrogel-cell composition" is a suspension of a hydrogel containing desired tissue precursor cells. These cells can be isolated directly from a tissue source or can be obtained from a cell culture. A "tissue" is a collection or aggregation of particular cells embedded within its natural matrix, wherein the natural matrix is produced by the particular living cells. A "living tissue construct" is a collection of living cells that have a defined shape and structure. To be "living," the cells must at least have a capacity for metabolism, but need not be able to grow or reproduce in all embodiments. Of course, a living tissue construct can also include, and in some embodiments preferably includes, cells that grow and/or reproduce.

"Tissue precursor cells" are cells that form the basis of new tissue. Tissue cells can be "organ cells," which include hepatocytes, islet cells, cells of intestinal origin, muscle cells, heart cells, cartilage cells, bone cells, kidney cells, cells of hair follicles, cells from the vitreous humor in the eyes, cells from the brain, and other cells acting primarily to synthesize and secret, or to metabolize materials. In some embodiments, these cells can be fully mature and differentiated cells. In addition, tissue precursor cells can be so-called "stem" cells or "progenitor" cells that are partially differentiated or undifferentiated precursor cells that can form a number of different types of specific cells under different ambient conditions, and that multiply and/or differentiate to form a new tissue.

An "isolated" tissue precursor cell, such as an isolated nerve cell, or an isolated nerve stem or progenitor cell or bone cell, or bone stem or progenitor cell, is a cell that has been removed from its natural environment in a tissue within an animal, and cultured in vitro, at least temporarily. The term covers single isolated cells, as well as cultures of "isolated" stem cells, that have been significantly enriched for the stem or progenitor cells with few or no differentiated cells.

As used herein, "negative mold" means a concave mold into which a liquid can be introduced for subsequent solidification. The mold is "negative" in the sense that concavity of the mold represents convexity in the object to be formed.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflicting subject matter, the present specification, including definitions, will control. In addition, the materials, methods, and examples are illustrative only and not intended to be limiting.

The invention has many advantages. For example, the new methods reduce the number of manufacturing steps needed to prepare precise, three-dimensional biological tissues. The new methods also provide increased uniformity of cell seeding throughout the construct, and increased efficiency of cell containment within the construct.

Other features and advantages of the invention will be apparent from the following detailed description, and from the claims.

BRIEF DESCRIPTION OF THE DRAWINGS

FIGS. 6A to 6C are a series of graphs showing glycosaminoglycan (GAG) content (FIG. 6A), hydroxyproline content (6B) and DNA content (6C) of molded constructs seeded at $10 \times 10^6$, $25 \times 10^6$, and $50 \times 10^6$ cells/ml and implanted subcutaneously in nude mice for 30 weeks. Each data point represents n=3+/−standard deviation. Correlation coefficients ($r^2$) and associated p values indicate levels of significance of changes in properties with seeding density.

FIGS. 7A and 7B are a series of graphs that illustrate compressive equilibrium modulus (FIG. 7A) and hydraulic permeability (7B) of molded constructs seeded at $10 \times 10^6$, $25 \times 10^6$, and $50 \times 10^6$ cells/ml and implanted subcutaneously in nude mice for 30 weeks. Each data point represents n=4+/−standard deviation. Correlation coefficients ($r^2$) and associated p values indicate levels of significance of changes in properties with seeding density.

DETAILED DESCRIPTION

Figure 1:
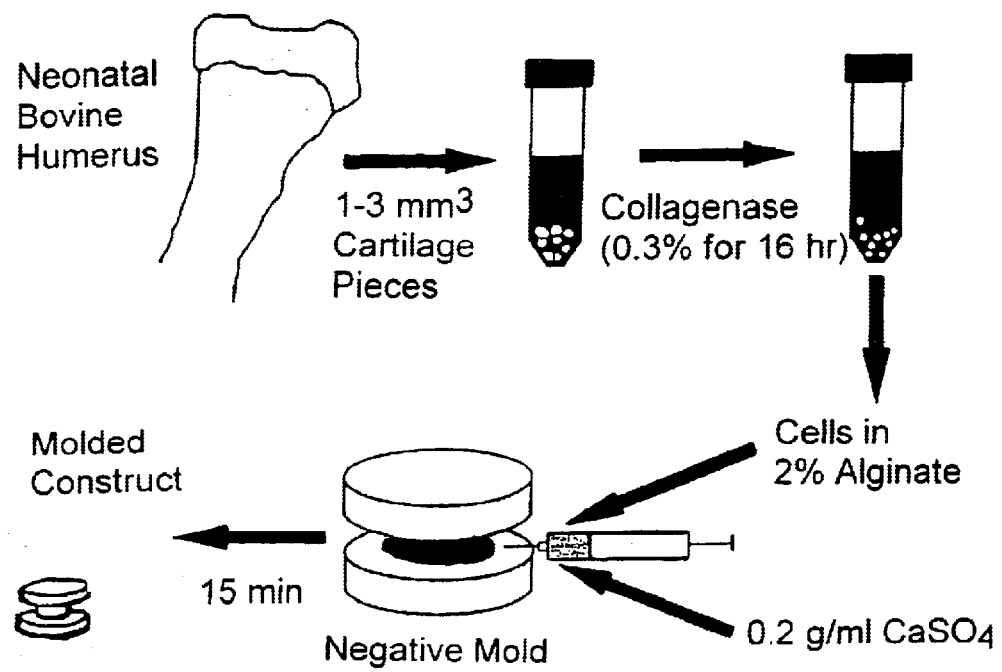
FIG. 1 is a schematic diagram of the injection molding process. Bovine articular cartilage was digested in collagenase II (3 mg/ml) at 37° C. for 12–18 hours. Chondrocytes were concentrated to 1, 2.5, and $5 \times 10^7$ cells/ml and suspended in a solution of 2% alginate. Immediately before injection into the mold, sterilized $CaSO_4$ (0.2 gm/ml of alginate) in PBS was mixed with chondrocytes in alginate to initiate gel formation. The chondrocyte/alginate/$CaSO_4$ mixture was injected to the sterilized mold using a syringe and needle. Formed shapes were removed from molds 15 minutes after injection.

The invention provides improved tissue engineering techniques and improved living tissue constructs or implants. In contrast to conventional tissue engineering techniques, that involve creating a shaped scaffold, and then seeding the shaped scaffold with cells in a separate step, the invention utilizes a suspension of cells in a solution from which a hydrogel is formed at a controlled gelation rate in the final shape of the tissue construct.

The new methods can be used to grow new tissue such as, for example, cartilage, bone, skin, epithelial layers, new organs, and central nervous system tissue, by using a hydrogel-cell composition that is formed into a precise shape using new injection molding techniques. To guide the development and shape of the new tissue, a precise negative mold is created, and the hydrogel-cell composition is delivered into the mold and cured to form a solid, three-dimensional living tissue construct, which is implanted into a patient after the hydrogel-cell composition is solidified. The construct can be first placed into an in vitro controlled environment to allow the cells to grow for a period of days or weeks within the solidified hydrogel, or the construct can be implanted directly after solidification. In the following subsections, suitable molding techniques, hydrogels, cells, and delivery methods will be described, along with illustrative examples.

General Methodology

As with any process based on injection molding, the size and shape of the shaped product is determined by the size and shape of the negative mold. Thus, the invention can be employed to produce a biological tissue implant or construct having essentially any size and shape, with the size and shape being precisely controlled. The living tissue construct can be used for the repair, reconstruction, or modification of external or internal anatomical structures. In some embodiments, the construct is a precisely shaped piece of cartilage for the reconstruction of an external anatomical structure, e.g., a nose or an ear. In other embodiments, the tissue construct is a precisely shaped piece of cartilage for the reconstruction of an internal anatomical structure such as a meniscus. In yet other embodiments, the biological implant is a precisely shaped piece of bone for the repair of a skeletal defect or injury. For example, pieces of bone can be produced for reconstruction of facial bones, following severe facial injuries in an automobile accident.

Because injection molding allows for the use of a precise negative mold, detailed anatomical information from MRI or CT devices can be utilized to maximum advantage. For example, data output from an MRI or CT device can serve as input for computer aided drafting/computer aided manufacturing (CAD/CAM) and rapid prototyping to produce high quality molds in which the biological tissue constructs are formed. CAD/CAM hardware and software are commercially available and can be employed using techniques known in the art, to design and produce molds suitable for use in the invention.

The principle of using MRI and CT data to fabricate custom-designed implants has been demonstrated using molded silicone (See, e.g., Binder and Kaye, 1994, Plast. Recon. Surg., 94:775–785). A similar procedure can be utilized as described here to produce custom-designed implants from living tissues such as cartilage or bone.

Although CAD/CAM techniques can be used in the design and production of molds they are not required. In some embodiments of the invention, a mold is constructed manually, e.g., by using a Silastic ERTV mold making kit (Dow Corning). For example, negative molds can be fabricated by immersing half of a positive model in a bed formed from the mixed components of an ERTV kit. This mixture is then placed in an 80° F. oven for 30 minutes. After the bottom is hardened, approximately the same amount of uncured silastic is poured on top to a height of 2 cm. This is again cured at 80° F. for 30 minutes. After separation of the top and lower sets of the mold, the model is removed.

As shown in FIG. 1, cells are extracted from a source, such as a bone or cartilage, using standard techniques. For example, cartilage can be cut into small pieces of 1 to 3 mm$^3$, and then disrupted with an enzyme or other chemical that separates the cells but does not destroy them. For example, collagenase works well for disrupting collagen into separate cells. The cells are then suspended in a hydrogel, such as 2% alginate, to produce a hydrogel-cell composition that can be delivered into the mold in liquid form, and is then injection molded into a pre-constructed negative mold. The hydrogel-cell composition is introduced into the mold simultaneously with a precise curing composition, such as 0.2 g/ml $CaSO_4$. After a predetermined time, such as 15 minutes for alginate, the hydrogel-cell composition is removed from the mold after it has solidified or cured.

Hydrogels

Any suitable polymer hydrogel can be used in methods of the invention. A suitable polymer hydrogel is one that is biologically compatible, non-cytotoxic, and formed through controllable crosslinking (gelation), under conditions compatible with viability of isolated cells suspended in the solution that undergoes gelation. Various polymer hydrogels meeting these requirements are known in the art and can be used in the practice of the invention. Examples of different hydrogels suitable for practicing this invention, include, but are not limited to: (1) hydrogels cross-linked by ions, e.g., sodium alginate; (2) temperature dependent hydrogels that solidify or set at body temperature, e.g., PLURONICS™; (3) hydrogels set by exposure to either visible or ultraviolet light, e.g., polyethylene glycol polylactic acid copolymers with acrylate end groups; and (4) hydrogels that are set or solidified upon a change in pH, e.g., TETRONICS™.

Examples of materials that can be used to form these different hydrogels include polysaccharides such as alginate, polyphosphazenes, and polyacrylates, which are crosslinked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

Ionic Hydrogels

Ionic polysaccharides, such as alginates and chitosan, can be used to suspend living cells. Tissue precursor cells are mixed with a polysaccharide solution, the solution is delivered into a mold, and then solidifies when the proper concentrations of ions are added. For example, alginate is an anionic polysaccharide capable of reversible gelation in the presence of an effective concentration of a divalent cation. A hydrogel can be produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

In a more specific example, $Ca^{++}$ can be supplied conveniently in the form of $CaSO_4$. In some embodiments of the invention, $CaSO_4$ is added in the amount of 0.1 to 0.5 gram, e.g., approximately 0.2 gram, per milliliter of a 2% solution of alginate. If the amount of soluble alginate is increased or decreased, the amount of divalent cation may need to be adjusted accordingly. Such adjustment is within ordinary skill in the art. The solubility of $CaSO_4$ is 0.209 g/ml, which is much lower than that of $CaCl_2$ (74.5 g/ml), which is the crosslinking agent typically used in for encapsulation of cells in alginate. See Beekman et al., 1997, Exper. Cell Res. 237:135–141. At a concentration of $CaSO_4$ near or above the solubility limit, $Ca^{2+}$ in solution begins to crosslink alginate, and it is replenished by solubilization of precipitated $CaSO_4$. This results in a significant slowing of the crosslinking process. Such slowing can be advantageous, because it allows the alginate/$CaSO_4$ mixture to be injected into a mold before the completion of the crosslinking process occurs in the shaped implant.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly (phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years and most preferably in less than about one year, once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described above are known to those skilled in the art. See, for example Concise Encyclopedia of Polymer Science and Engineering, J. I. Kroschwitz, editor (John Wiley and Sons, New York, N.Y., 1990). Many polymers, such as poly(acrylic acid), alginates, and PLURONICS™, are commercially available.

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels.

Anions for cross-linking the polymers to form a hydrogel include divalent and trivalent anions such as low molecular weight dicarboxylate ions, terepthalate ions, sulfate ions, and carbonate ions. Aqueous solutions of the salts of these anions are added to the polymers to form soft, highly swollen hydrogels, as described with respect to cations.

For purposes of preventing the passage of antibodies into the hydrogel, but allowing the entry of nutrients, a useful polymer size in the hydrogel is in the range of between 10,000 D and 18,500 D. Smaller polymers result in gels of higher density with smaller pores.

Temperature-dependent Hydrogels

Temperature-dependent, or thermosensitive, hydrogels can be use in the methods of the invention. These hydrogels have so-called "reverse gelation" properties, i.e., they are liquids at or below room temperature, and gel when warmed to higher temperatures, e.g., at or above body temperature. Thus, these hydrogels can be easily injected into a mold at or below room temperature as a liquid and automatically form a semi-solid gel when warmed to or above body temperature. Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers.

These copolymers can be manipulated by standard techniques to affect their physical properties such as porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration. These gels have diffusion characteristics capable of allowing cells to survive and be nourished.

U.S. Pat. No. 4,188,373 describes using PLURONIC™ polyols in aqueous compositions to provide thermal gelling aqueous systems. U.S. Pat. Nos. 4,474,751, '752, '753, and 4,478,822 describe drug delivery systems which utilize thermosetting polyoxyalkylene gels; with these systems, both the gel transition temperature and/or the rigidity of the gel can be modified by adjustment of the pH and/or the ionic strength, as well as by the concentration of the polymer.

pH-Dependent Hydrogels

Other hydrogels suitable for use in the methods of the invention are pH-dependent. These hydrogels are liquids at, below, or above specific pH values, and gel when exposed to specific pHs, e.g., 7.35 to 7.45, the normal pH range of extracellular fluids within the human body. Thus, these hydrogels can be easily delivered into a mold as a liquid and form a semisolid gel when exposed to the proper pH. Examples of such pH-dependent hydrogels are TETRONICS™ (BASF-Wyandotte) polyoxyethylene-polyoxypropylene polymers of ethylene diamine, poly (diethyl aminoethyl methacrylate-g-ethylene glycol), and poly(2-hydroxymethyl methacrylate). These copolymers can be manipulated by standard techniques to affect their physical properties.

An example of another a useful pH-dependent hydrogel is collagen. Collagen is a protein that undergoes cross-linking in response to shift in pH from alkaline to acid, e.g., a shift from a pH in the range of <2 to a pH in the range of >6. See, e.g., Bell et al., 1979, Proc. Nat. Acad. Sci., 76:1274.

Light Solidified Hydrogels

Other hydrogels that can be used in the methods of the invention are solidified by either visible or ultraviolet light. These hydrogels are made of macromers including a water-soluble region, a biodegradable region, and at least two polymerizable regions as described in U.S. Pat. No. 5,410,016. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light. These types of hydrogels can be used with transparent or translucent molds, or with molds that have optic fibers that introduce light into the mold.

Examples of such light solidified hydrogels include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

Tissue Precursor Cells

Various types of isolated cells or tissue precursor cells (e.g., progenitor or stem cells) can be used in methods according to the invention. Selection of cell type will depend on the type of construct to be produced. For example, isolated chondrocytes are used for production of a shaped cartilage tissue construct. Isolated osteocytes are used for production of shaped bone constructs. Isolated adipocytes are used for production of shaped adipose tissue constructs. Myoblasts are used for production of a shaped muscle tissue constructs.

Tissue precursor cells can be obtained directly from a mammalian donor, e.g., a patient's own cells, from a culture of cells from a donor, or from established cell culture lines. Preferably the mammal is a mouse, rat, rabbit, guinea pig, hamster, cow, pig, horse, goat, sheep, dog, cat, and most preferably, the mammal is a human. Cells of the same species and preferably of the same immunological profile can be obtained by biopsy, either from the patient or a close relative. Using standard cell culture techniques and conditions, the cells are then grown in culture until confluent and used when needed. The cells are preferably cultured only until a sufficient number of cells have been obtained for a particular application.

If cells are used that may elicit an immune reaction, such as human muscle cells from an immunologically distinct donor, then the recipient can be immunosuppressed as needed, for example, using a schedule of steroids and other immunosuppressant drugs such as cyclosporine. However, the use of autologous cells will avoid such an immunologic reaction.

Cells can be obtained directly from a donor, washed, suspended in a selected hydrogel before being injected into a mold. To enhance cell growth, the cells are added or mixed with the hydrogel just prior to injection into the mold. Cells obtained by biopsy are harvested, cultured, and then passaged as necessary to remove contaminating, unwanted cells. The isolation of chondrocytes is described in the examples below. Cell viability can be assessed using standard techniques including visual observation with a light or scanning electron microscope, histology, or quantitative assessment with radioisotopes. The biological function or metabolism of the cells can be determined using a combination of the above techniques and standard functional assays.

Examples of cells that can be delivered into molds and subsequently grow new tissue in living tissue constructs include epidermal cells; chondrocytes and other cells that form cartilage ("cartilage-forming cells"); macrophages; dermal cells; muscle cells; hair follicles; fibroblasts; organ cells; osteoblasts, periosteal cells, and other cells that form bone ("bone forming cells"); endothelial cells; mucosal cells, e.g., nasal, gastric, bladder and oral mucosal cells; pleural cells; ear canal cells; tympanic membrane cells; peritoneal cells; Schwann cells; corneal epithelial cells; gingiva cells; tracheal epithelial cells; and neural cells, including neuronal stem cells and neurons.

Preparation of Hydrogel-Cell Compositions

First, a hydrogel of choice is prepared using standard techniques. For example, a biodegradable, thermosensitive polymer at a concentration ranging between 5 and 25% (WV) is useful for the present invention. If the hydrogel is an alginate, it can be dissolved in an aqueous solution, for example, a 0.1 M potassium phosphate solution, at physiological pH, to a concentration between about 0.1 to about 4% by weight, e.g., 2%, to form an ionic hydrogel.

Second, isolated tissue precursor cells are suspended in the polymer solution at a concentration mimicking that of the tissue to be generated. The optimal concentration of cells to be delivered into the mold is determined on a case by case basis, and may vary depending on cellular type and the region of the patient's body into which the living tissue implant is inserted. Optimization experiments require modifying only a few parameters, i.e., the cell concentration or the hydrogel concentration, to provide optimal viscosity and cell number to support the growth of new tissue. For chondrocytes, the cell concentration range is from about 10 million cells/ml to about 100 million cells/ml, e.g., from about 25 million cells/ml to about 50 million cells/ml.

Implantation of Living Tissue Constructs

To implant a living tissue construct, the implantation site of the mammalian patient can be exposed by surgical resection and the construct implanted directly at that site. Alternatively, if the construct is small enough, the implantation site can be viewed with the aid of, e.g., an endoscope, laparoscope, arthroscope, or esophagoscope, all of which can be modified to include a mechanical articulation and delivery system for implanting the tissue construct through a small incision. During implantation, the site is cleared of bodily fluids including blood, e.g., with a burst of air or suction. Thus, the hydrogel-cell-containing tissue construct can be introduced through a laparoscope, endoscope, laryngoscope, cystoscope, proctoscope, or thoracoscope to any the interior surface of any lumen or cavity, or other surfaces, such as intraperitoneal, extraperitoneal, and thoracic cavity, and then implanted into the desired space.

Throughout the implantation procedure, the amount of trauma caused to the cells during the delivery and implantation steps can be determined by measuring a biological function specific for the cells being used. For example, when chondrocytes are being applied, the integrity of the new cartilage can be evaluated by standard biomechanical stress analyses, such as determination of compression moduli.

Applications

Since the hydrogel-cell compositions can support many different kinds of tissue precursor cells and the injection molding methods can be used to create virtually any three-dimensional shape, the new methods can be used in any instance in which it desirable to generate new tissue. Particular applications that are described below relate to the generation of cartilage, bone, and neural tissues.

Treatment of Cartilage Defects

Cartilage is a specialized type of dense connective tissue consisting of cells embedded in a matrix. There are several kinds of cartilage. Hyaline cartilage is a bluish-white, glassy translucent cartilage having a homogeneous matrix containing collagenous fibers that is found in articular cartilage, in costal cartilages, in the septum of the nose, and in the larynx and trachea. Articular cartilage is hyaline cartilage covering the articular surfaces of bones. Costal cartilage connects the true ribs and the sternum. Fibrous cartilage contains collagen fibers. Yellow cartilage is a network of elastic fibers holding cartilage cells which is found primarily in the epiglottis, the external ear, and the auditory tube. By harvesting the appropriate chondrocyte precursor cells, any of these types of cartilage tissue can be grown using the methods of the invention.

For example, new tissue can be grown for a cartilage meniscus replacement in the knee. A negative mold is prepared to provide a tissue construct in the shape of the meniscus to be replaced. Thereafter, a liquid hydrogel-chondrocyte composition is injected into the mold. The hydrogel subsequently solidifies, taking the shape of the desired meniscus replacement and providing a suspension for the chondrocytes that permits diffusion of nutrients and waste products to and from the suspended chondrocytes. After solidifying, the new tissue construct is implanted into the knee using the standard surgical techniques. Over time, e.g., over a period of approximately six weeks, the construct will become vascularized and the chondrocytes will grow new cartilaginous tissue that takes the shape of the meniscus and engrafts to existing tissue.

Treatment of Bone Defects

In another example, periosteal cells (i.e., bone-growing cells) can be used in the invention to fill bone defects or to prepare entire new bones. First, a negative mold is prepared to fit the dimensions of the bone defect (e.g., by creating a positive model of the bone defect with a plastic materials that is filled into the defect while in paste or gel form and then solidifies). The negative mold is prepared from the plastic positive model. The hydrogel-periosteal-cell composition can then be delivered into the mold. Once again the hydrogel solidifies, i.e., suspends and maintains the cells. After the tissue construct is solidified, it is implanted into the bone defect and subsequently grows bone tissue to fill in the bone defect.

In order that the invention may be more fully understood, the following examples are provided. The examples are for illustrative purposes only, and they are not to be construed as limiting the scope or content of the invention in any way.

EXAMPLES

Experiments were conducted to develop methods to create structures of complex geometry to form cartilage in specific shapes. Several standard facial implants (nose bridge, chin, malar, and nasal septum) were used as templates and chondrocyte/alginate constructs were molded in these shapes (see FIGS. 2A and 2B). After subcutaneous implantation, these constructs developed morphology that closely resembled that of native cartilage. Constructs also showed increases in content of proteoglycan and collagen, the two major constituents of the cartilage extracellular matrix. The mechanical properties of constructs continued to evolve with time, showing increasing equilibrium modulus and decreasing hydraulic permeability, consistent with greater mechanical integrity of the tissue.

Example 1

Isolation of Chondrocytes

Due to the large number of cells (~$10^{10}$ chondrocytes) needed for this study, bovine articular cartilage was chosen as the tissue source because of its availability. Freshly slaughtered calf forelimbs were obtained from a local slaughterhouse within 6 hours of sacrifice. The forelimbs were dissected under sterile conditions to expose the articular surfaces of the glenohumeral and humeroulnar joint. Cartilage fragments were sharply curetted off the articular surface of each joint, were subjected to collagenase II digestion (3 mg/ml) (Worthington Biochemical Corp, freehold, N.J. USA.) at 37° C. for 12 to 18 hours. Preparation of chondrocytes was in accordance with methods described in Klagsburn, 1979, Meth. Enzymol., 58:560–564.

The resulting cell suspension was passed through a sterile 250 ì polypropylene mesh filter (Spectra/Mesh 146-426 Spectrum Medical Industries, Inc., Laguna Hills, Calif., and USA.). The filtrate was centrifuged at 6000 rpm, and the resulting cell pellet was washed twice with copious amounts of Dulbecco phosphate buffered-saline (PBS) (Gibco, Grand Island, N.Y., USA) without $Ca^{2+}$. Cell number was determined using a hemocytometer and the cell viability determined using trypan blue dye (Sigma-Aldrich, Irvine, Kans., USA.). Chondrocyte suspensions were concentrated to various cellular densities of 10, 25, and $50\times10^6$ cells/ml and suspended in a solution of 2% alginate.

Example 2

Construction of Molds

Molds were prepared using silicone chin implants or nose bridges (Implantech, Ventura, Calif.) as positive models for use with a Silastic ERTV mold making kit (Dow Corning). The two components of the ERTV kits were mixed and poured into the bottom of a 100 ml beaker to a height of 2 cm. The silicone implant was embedded in the ERTV mixture and the beaker was placed in an 80° F. oven for 30 minutes. After the bottom was hardened, approximately the same amount of uncured silastic was poured on top to a height of 2 cm. This was again cured at 80° F. for 30 minutes. After separation of the top and lower sets of the mold, the silicon implant was removed.

Example 3

Alginate Construct Formation

Isolated cells were resuspended in a 2% sterile sodium alginate (Pronova Biopolymer, Norway) solution (0.1M $K_2HPO_4$, 0.135M NaCl, pH 7.4), which had previously been sterilized with a 0.45 nm filter to yield various cellular concentrations of 10, 25, and $50\times10^6$/ml alginate solution. Immediately before injection into the silicon mold, sterilized $CaSO_4$ (0.2 gm/ml of alginate solution) in PBS solution was mixed with chondrocyte-alginate construct to initiate gel formation. The chondrocyte/alginate/$CaSO_4$ mixture was delivered to the sterilized mold using a 10 ml syringe and an 18.5 gauge needle. Formed shapes were removed from molds 10 minutes after injection. FIG. 1 illustrates the overall method.

Figure 2A:
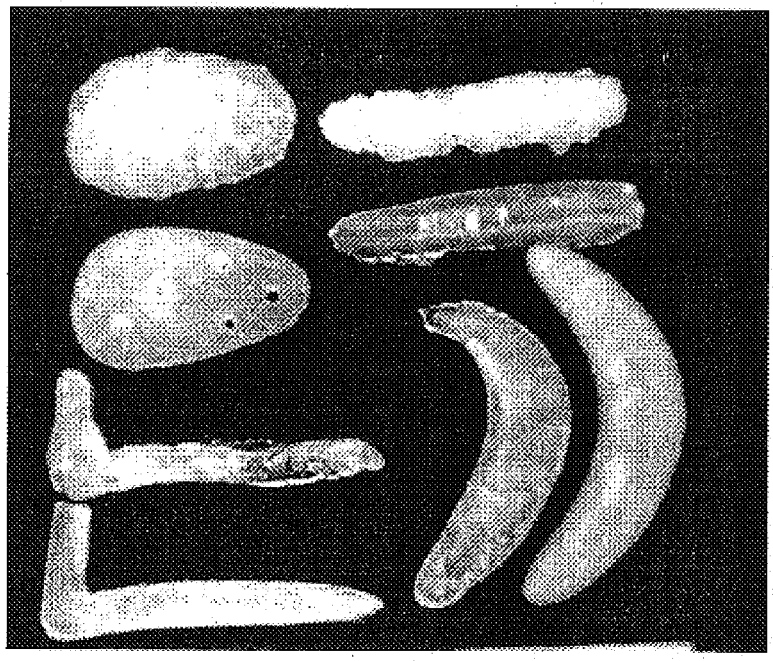
FIG. 2A is an illustration of a silicone and corresponding alginate nose bridge (pair of structures in upper left), a silicone and a corresponding alginate chin implant (crescent-shaped pair in lower right), a silicone and alginate malar implant (L-shaped pair in lower left), and a silicone and alginate nasal septum implants (elongate pair in upper right). In these figures, the silicone is gray and clear, and the alginate is white and opaque.
Figure 2B:
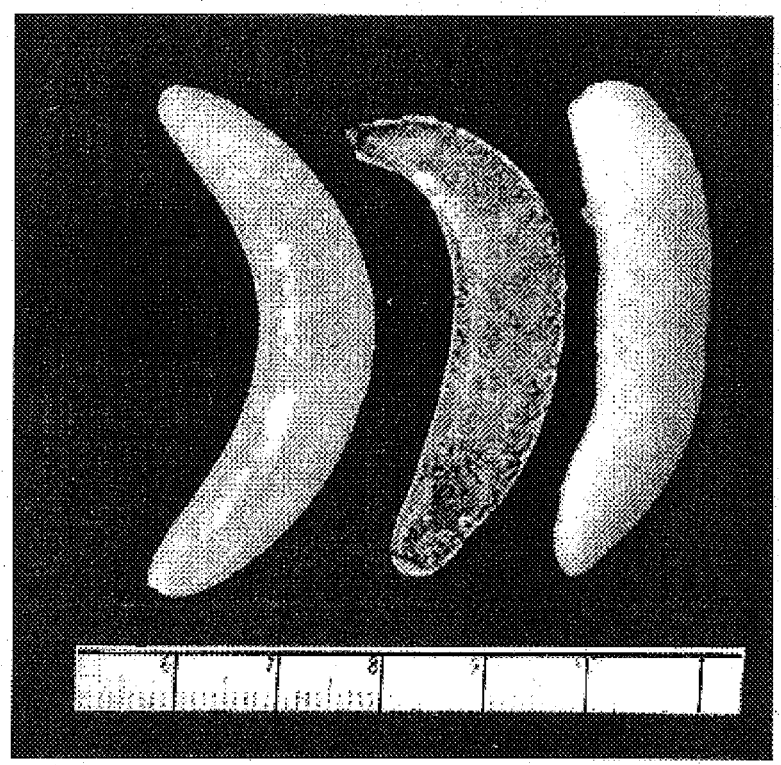
FIG. 2B is an illustration of a silicone chin implant (left), a corresponding molded alginate construct (middle), and resultant cartilage (right) removed 30 weeks after implantation into the subcutaneous space of a nude mouse.

Using the molding method, chondrocyte/alginate constructs were formed in the shape of a nose bridge, chin implant, malar implant, and L-shaped nose implants (Implant Technologies). A total of 28 constructs seeded at a density of $50\times10^6$ cells/ml (50 million/ml) were implanted subcutaneously in the dorsal aspect of 14 nude mice and harvested at 2, 4, 6, 8, 10, 12, and 30 weeks. In a parallel study, 12 constructs were seeded at 10, 25, and $50\times10^6$ cells/ml, then were implanted in the dorsal aspect of 6 nude mice and harvested at 30 weeks. Various shaped alginate/cell constructs (nose bridge, and chin) have been produced using this method (FIGS. 2A and 2B). The alginate or alginate/cell constructs were formed quickly, easily, and reproducibly into specific shapes. Cell viability after 24 hours in culture was >85%. The shape of the constructs immediately after removal from the mold and after retrieval from in vivo implantation was very similar to the original model.

Example 4

Analysis of Cartilage Tissue Constructs

The development of cartilage in vivo in the constructs after implantation was analyzed over time. More specifically, both biochemical and biomechanical properties of the constructs were monitored to determine any changes with time and seeding density. To analyze these results, the linear correlation coefficient ($r^2$) was calculated for changes in GAG, hydroxyproline, DNA, equilibrium modulus, and hydraulic permeability with time and with seeding density using Microsoft Excel software. This value of $r^2$ for each parameter was compared to a critical value for the number of samples in the study to determine statistical significance (p value).

Figure 3A:
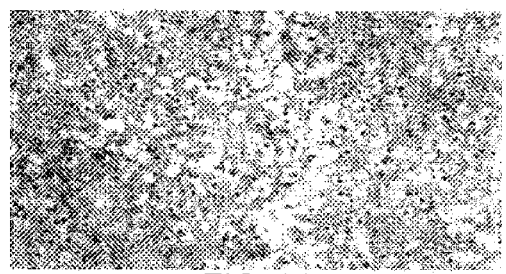
FIGS. 3A to 3G are photomicrographs of Safranin-O staining of nasal constructs (100×) at 2 weeks (FIG. 3A), 4 weeks (3B), 6 weeks (3C), and 12 weeks (3D) after retrieval from subcutaneous implantation. Hematoxylin and eosin staining (200×) of nasal constructs seeded at $10 \times 10^6$ cells/ml (FIG. 3E), $25 \times 10^6$ cells/ml (3F), $50 \times 10^6$ cells/ml (3G) and implanted subcutaneously for 30 weeks.
Figure 3B:
Figure 3C:
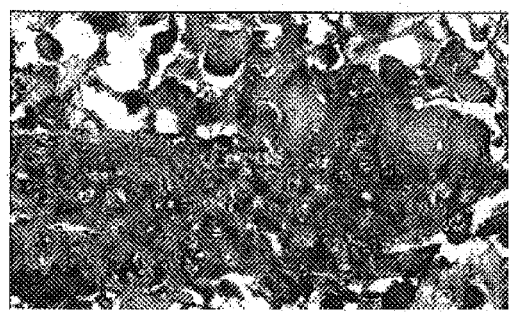
Figure 3D:
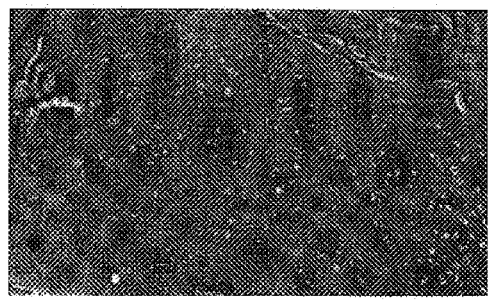
Figure 3E:
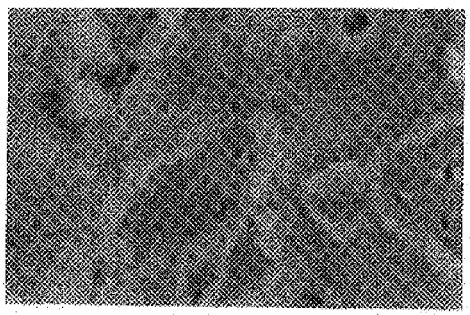
Figure 3F:
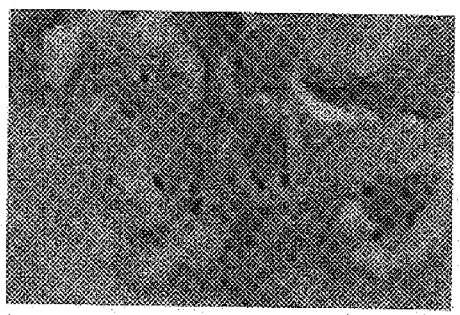
Figure 3G:
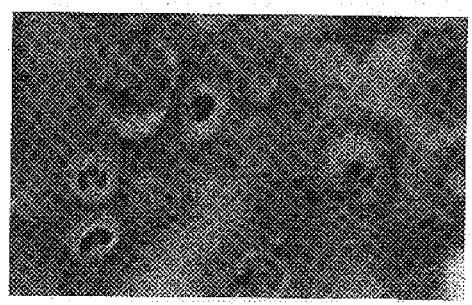

Upon removal, samples were either fixed in formalin for histological examination or frozen at $-80°$ C. for biomechanical and biochemical evaluation. Specifically, after fixation with 10% phosphate-buffered formalin for at least 24 hours, specimens were embedded within paraffin and sectioned. Using standard histochemical techniques, serial sections were stained with H & E (Hematoxylin and eosin) and Safranin-O stains. Histology of two-week samples indicated the presence of a high concentration of cells with rounded morphology consistent with that of the chondrocyte phenotype (FIG. 3A). Slight staining with Safranin-O indicated a low concentration of proteoglycan. By 4 weeks, cellular and pericellular regions stained heavily for Safranin-O, indicating the presence of islands of cartilage forming within the specimens (FIG. 3B). By 6 weeks, multiple islands of cartilage have joined together (FIG. 3C), and, at 12 weeks, the formation of a solid piece of cartilage is evident, with Safranin-O staining throughout the sample (FIG. 3D). This 12 weeks time scale was consistent with the known degradation time for alginate in subcutaneous space (See, Suzkuki et al., 1999, J. Biomed. Mat. Res., 48:522–527). Seeding density had very little effect on the cellular and tissue morphology in cartilage specimens at 30 weeks (FIGS. 3E–G). Hematoxylin and eosin staining revealed consistently rounded morphology for cells seeded into implants at 10, 25 and $50×10^6$ cells/ml.

Alternatively, samples of engineered cartilage stored at $-80°$ C. were cut to approximately 1 mm thick by using a razor blade and a 6-mm diameter dermal punch. Each disk was immediately mounted in an electrically insulating cylindrical confining chamber. The chamber was mounted in a servo-controlled Dynastat® mechanical spectrometer (IMASS, Hingham, Mass.) interfaced to a computer e.g., as described in (Bonassar et al., 1995, Arthritis Rheum., 38:1678–1686). The samples were equilibrated at room temperature in 0.15 M PBS, pH 7.4, containing 100 units/ml penicillin G and 100 îg/ml streptomycin. Samples were compressed between a porous polyethylene platen and at the base of the chamber.

After mounting each disk in the confined compression chamber, the distance between the porous platen and the chamber was decreased until a signal of ~5 gm (50 mN) was detected by the load cell. This distance was taken to be the sample thickness. Each disk was compressed by 10 sequential increments of 2.5–3.0% static strain, up to a maximum of 25–30% total strain. After each increment, the load was recorded every 0.5 seconds for 100 seconds. Stress relaxation data was fit to a poroelastic model of material behavior that yielded values for the material properties, equilibrium modulus and hydraulic permeability (Mow et al., 1980, J. Biomech. Eng., 102:73–84; Quinn et al., 1993, Macromolecules, 26:4332–4338).

Figures 5A, 5B:
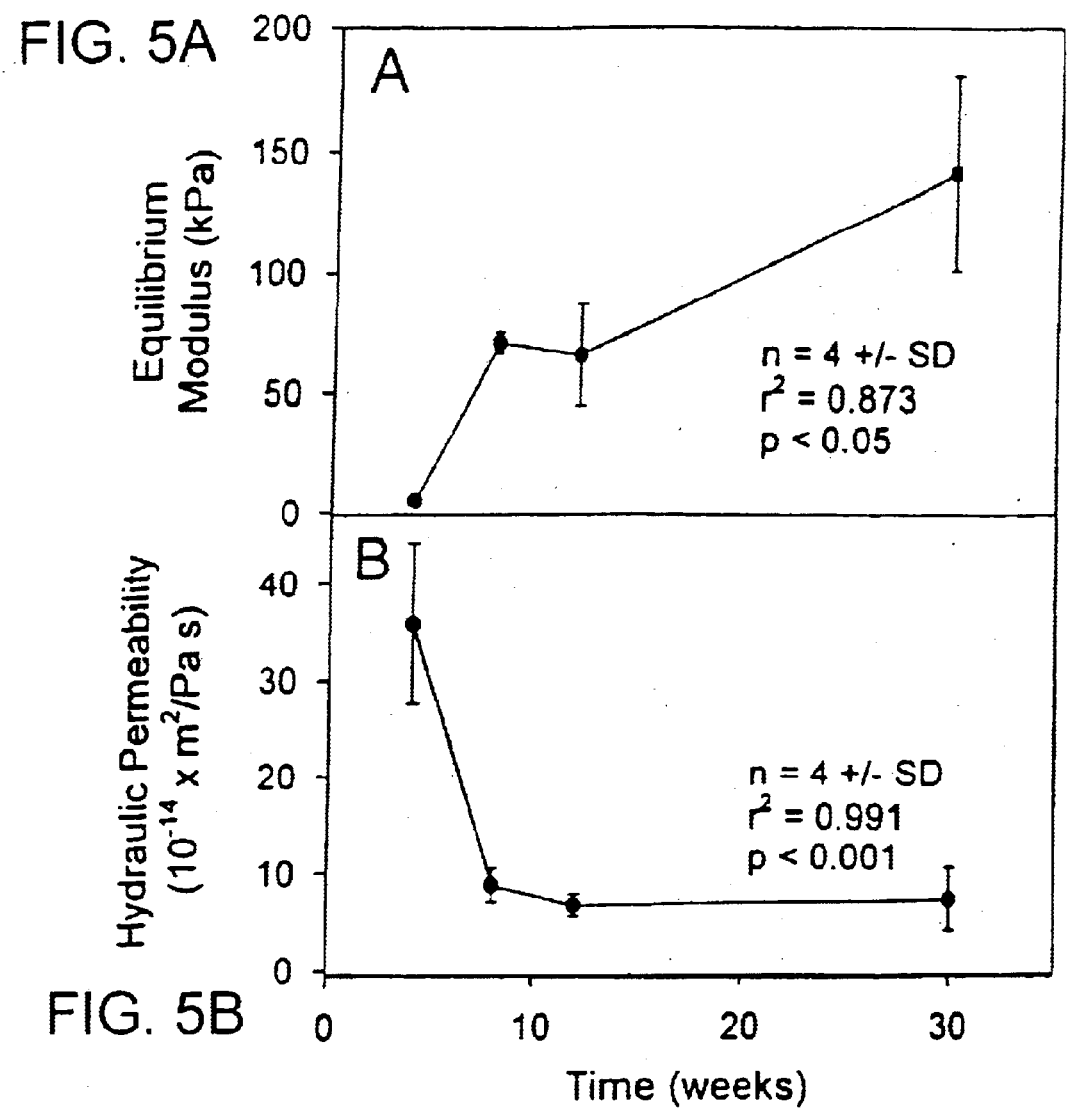
FIGS. 5A and 5B are a series of graphs showing compressive equilibrium modulus (FIG. 5A) and hydraulic permeability (5B) of various molded constructs seeded at $50 \times 10^6$ cells/ml and implanted subcutaneously in nude mice and removed at 4, 8, 12, and 30 weeks. Each data point represents n=3+/−standard deviation. Correlation coefficients ($r^2$) and associated p values indicate levels of significance of changes in properties with time.

Evaluation of mechanical properties indicated that equilibrium modulus increased with time in vivo ($p<0.02$) from 5+/−4 kPa to 140+/−40 kPa at 30 weeks (FIG. 5A), to approximately 15% of the aggregate modulus (0.99+/−0.5 MPa) of native bovine articular cartilage (Mow et al., 1980, J. Biomech. Eng., 102:73–84), and 60% of that of human nasal cartilage (234±27 kPa) (Stockwell et al., 1979, "The Chondrocyte" in Adult Articular Cartilage, Pitman Medical, UK). In contrast, hydraulic permeability ($m^2$/Pa s) decreased ($p=0.02$) with time in culture from $4.1×10^{-12}$ $m^2$/Pa s to $6.6×10^{-14}$ $m^2$/Pa s at 30 weeks (FIG. 5B), which is about 20 times higher than that of native bovine articular cartilage ($3×10^{-15}$ $m^2$/Pa s), and twice that of human nasal cartilage ($6.0×10^{-14}±0.8×10^{-14}$). Thus, while the mechanical properties of the new implants in these studies did not match the properties are of articular cartilage, they are similar to that of other facial cartilage. The modulus increased significantly with seeding density in vivo (FIG. 7A), while permeability decreased significantly ($p<0.05$) with seeding density (FIG. 7B).

After biomechanical analysis, samples were weighed on a microbalance to 0.0001 gram, and digested by addition of 1.34 ml of 55 mM sodium citrate (BDH), 150 mM sodium chloride (BDH), 5 mM cysteine hydrochloride (Sigma), 5 mM EDTA (BDH), and 0.56 units/ml papain (Sigma). The samples were incubated at $60°$ C. for 24 hours. The digest was stored at $-70°$ C. At 30 weeks in vivo, the weights of harvested samples increased with cell concentration (10, 25, 50 millions/ml: mean weights: 0.64+−0.022, 0.98+−0.041, 1.56+−0.056 mg). The DNA concentrations in all cellpolymer constructs increased with higher cellular concentration in vivo ($p<0.05$) (FIG. 6C).

The sulfated glycosaminoglycan (GAG) content of digests was quantified according to known methods (Beekman et al., 1997, Exp. Cell Res,. 237:135–141; Enobakhare et al., 1996, Anal. Biochem,. 243:189–191). Briefly, 10 îl of papain digest was added to 200 îl of DMB (1,9-dimethylmethylene blue) dye at pH 2 to minimize the reaction of the dye with the alginate. Absorbances was detected at 595 nm with a spectrophotometer immediately after addition of the dye. GAG content of the samples was determined using a C-6-S from shark cartilage (Sigma) as a standard. The hydroxyproline contents of digests were determined by the procedure of Stegeman and Stadler (1967, Clin. Chim. Acta, 18:267–273). The papain digests were hydrolyzed with equal volumes of 6N HCl in $115°$ C. for 16–24 hours. Chloramine T and p-dimethyl-aminobenzaldehyde were added to hydrolyzed samples and absorbances were detected at 560 nm with a spectrophotometer immediately after addition of the dye.

Figures 4A, 4B, 4C:
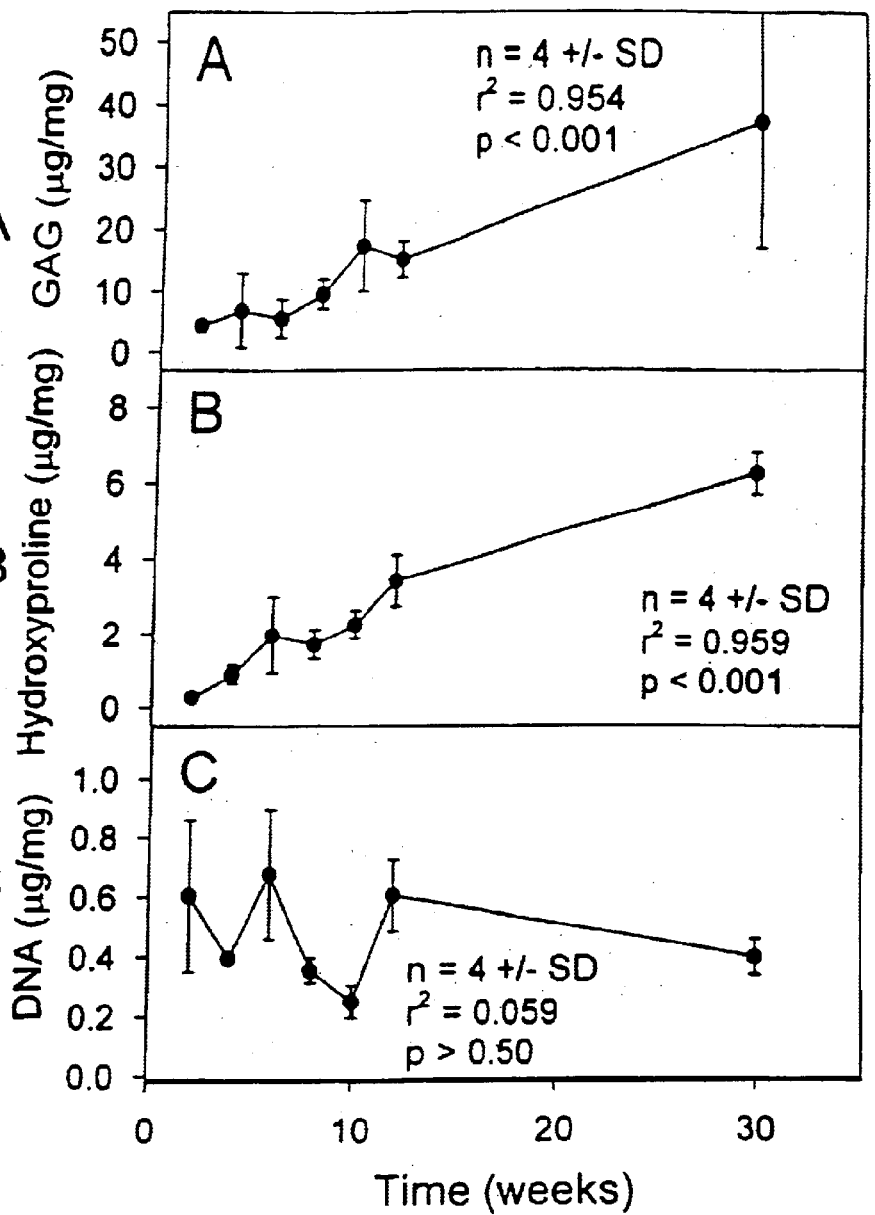
FIGS. 4A to 4C are a series of graphs showing the glycosaminoglycan (GAG) content (FIG. 4A), hydroxyproline content (4B), and DNA content (4C) of various molded constructs seeded at $50 \times 10^6$ cells/ml and implanted subcutaneously in nude mice and removed at 2, 4, 6, 8, 10, 12, and 30 weeks. Each data point represents n=4+/−standard deviation. Correlation coefficients ($r^2$) and associated p values indicate levels of significance of changes in properties with time.

The glycosaminoglycan and hydroxyproline contents increased significantly ($p<0.001$) with time in vivo (FIGS. 4A and 4B). By 30 weeks, GAG content was 39+/−2.5 $\mu$g/mg (721 ng/cell)(FIG. 4A), approximately 60% of that of native bovine articular cartilage (70.5+/−5.6 îg/mg). Hydroxyproline content of implants at 30 weeks was 6.3+/− 0.5 îg/mg (116 ng/cell)(FIG. 4B), which is 70% of that of normal tissue (9+/−0.5 îg/mg). Glycosaminoglycan and hydroxyproline content of constructs, increased with higher seeding density ($p<0.05$) (FIGS. 6A and 6B).

DNA content of samples was determined by quantitating fluorescence (358/458 nm) of aliquots immediately after mixing with bisbenzimidazole dye (Hoechst 33258) using a fluorimeter (Kim et al., 1988, Anal. Biochem., 174:168–176). The DNA content of cellpolymer constructs showed some variation, from 0.32 to 0.71 îg/mg, but remained relatively constant (FIG. 4C), showing no statistically significant change over 30 weeks, and resembled that of native bovine articular cartilage (0.375+/−0.012 ig/mg). Thus, the biochemical and cellular composition of tissue engineering cartilage in shaped implants is similar to that of native cartilage (Genes et al., 1999, ASME Proc. Bioeng., 42:1).

Cartilage formation was observed microscopically in specimens with a cellular density as low as 10 million chondrocytes/ml. Three cell concentrations used in this study were in the range of that of native tissue (10 to 100×10$^6$ cells/ml). Matrix assembly and mechanical properties were dependent on seeding density (FIGS. 6A–C and 7A–B), with the highest concentration, 50 million/ml, generating the highest quality tissue, as indicated by histology, biochemical analysis and biomechanical examination.

OTHER EMBODIMENTS

A number of embodiments of the invention have been described. Nevertheless, it will be understood that various modifications may be made without departing from the spirit and scope of the invention.

What is claimed is:

1. A method of making a living tissue construct having a predetermined shape, the method comprising providing a negative mold having a defined shape, wherein the negative mold is prepared using computer aided drafting/computer aided manufacturing (CAD/CAM) or rapid prototyping;

suspending isolated tissue precursor cells in a hydrogel to form a liquid hydrogel-precursor cell composition;

introducing the liquid hydra gel-precursor cell composition into the mold;

inducing gel formation to solidify the liquid hydrogel-precursor cell composition to form a living tissue construct; and removing the living tissue construct from the mold after gel formation.

2. The method of claim 1, wherein the tissue precursor cells are chondrocytes, osteocytes, osteoblasts, or adipocytes, or a combination thereof.

3. The method of claim 1, wherein the tissue precursor cells are chondrocytes.

4. The method of claim 1, wherein the hydrogel is selected from the group consisting of alginate, chitosan, pluronic, collagen, and agarose.

5. The method of claim 1, wherein the hydrogel is alginate.

6. The method of claim 5, wherein the alginate concentration is from 0.5% to 8%.

7. The method of claim 5, wherein the alginate Concentration is from 1% to 4%.

8. The method of claim 5, wherein the alginate concentration is approximately 2%.

9. The method of claim 1, wherein inducing gel formation comprises contacting the liquid hydrogel with a suitable concentration of a divalent cation.

10. The method of claim 9, wherein the divalent cation is Ca++.

11. The method of claim 10, wherein the suitable concentration of Ca ion is 0.2 g/ml of the liquid hydrogel-precursor cell composition.

12. The method of claim 1, further comprising culturing the tissue precursor cells in the solidified hydrogel for a period of 1 to 30 days.

13. An injection-molded living tissue construct made by the process of claim 1.

14. A method of reconstructing an anatomical feature in a mammal, the method comprising obtaining a living tissue construct having the shape of the anatomical feature; and implanting the tissue construct into the mammal, wherein the construct is prepared by the method of claim 1.

15. The method of claim 1, wherein the living tissue construct is shaped in the form of articular cartilage adjacent a joint, a bone, a portion of a bone, or a bone defect.

16. The method of claim 1, wherein the hydrogel is selected from the group consisting of polysaccharides, proteins, polyphosphazenes, poly(oxyethylene)-poly (oxypropylene) block polymers, poly(oxyethylene)-poly (oxypropylene) block polymers of ethylene diamine, poly (acrylic acids), poly(methacrylic acids), copolymers of acrylic acid and methacrylic acid, poly(vinyl acetate), and sulfonated polymers.

17. The method of claim 1, wherein the tissue precursor cells are selected from the group consisting of epidermal cells, chondrocytes and other cells that form cartilage, macrophages, dermal cells, muscle cells, hair follicles, fibroblasts, organ cells, osteoblasts and other cells that form bone, endothelial cells, mucosal cells, pleural cells, ear canal cells, tympanic membrane cells, peritoneal cells, Schwann cells, corneal epithelial cells, gingiva cells, neural cells, neural stem cells, and tracheal epithelial cells.

18. The method of claim 1, wherein the tissue precursor cells are nervous system neural stem or progenitor cells.

19. The method of claim 1, further comprising implanting the tissue construct into a mammal.

20. A method of making a living tissue construct having a predetermined shape, the method comprising providing a negative mold having a defined shape;

suspending isolated tissue precursor cells in a hydrogel to form a liquid hydrogel-precursor cell composition;

introducing the liquid hydrogel-precursor cell composition into the mold;

inducing gel formation to form a living tissue construct, wherein inducing gel formation comprises contacting the liquid hydrogel with $Ca^{2+}$ at a concentration of 0.2 g/ml in the liquid hydrogel-precursor cell composition; and removing the living tissue construct from the mold after gel formation.

* * * * *